United States Patent [19]

Dessau et al.

[11] 4,442,210

[45] Apr. 10, 1984

[54] PROCESS FOR THE PRODUCTION OF FERMENTATION ETHANOL

[75] Inventors: Ralph M. Dessau, Edison; Werner O. Haag, Lawrenceville, both of N.J.

[73] Assignee: Mobil Oil Corporation, New York, N.Y.

[21] Appl. No.: 298,665

[22] Filed: Sep. 2, 1981

[51] Int. Cl.³ .............................................. C12P 7/06
[52] U.S. Cl. ..................................... 435/161; 435/801
[58] Field of Search .............. 435/161, 162, 165, 311, 435/247, 801; 585/408, 640

[56] References Cited

U.S. PATENT DOCUMENTS

| | | | |
|---|---|---|---|
| 2,440,925 | 5/1948 | Boeckeler | 435/162 |
| 2,474,170 | 6/1949 | Sulzbacher | 435/161 X |
| 2,476,785 | 7/1949 | Wallerstein | 435/161 |
| 3,000,792 | 9/1961 | Denkewalter et al. | 435/75 |
| 3,551,297 | 12/1970 | Hosler | 435/311 X |
| 3,702,886 | 11/1972 | Argauer et al. | 435/328 |
| 3,732,326 | 5/1973 | Chen | 210/691 X |
| 3,898,959 | 8/1975 | Chen et al. | 435/311 X |

*Primary Examiner*—R. B. Penland
*Attorney, Agent, or Firm*—Alexander J. McKillop; Michael G. Gilman; Laurence P. Hobbes

[57] ABSTRACT

Ethanol is recovered from a fermentation mixture by contact with a crystalline zeolite sorbent exemplified by ZSM-5, followed by desorption of concentrated ethanol. In one embodiment of this invention, the sorption step is conducted during fermentation to maintain the ethanol concentration in the fermenting mixture at a concentration below that which is toxic to the fermenting organism.

28 Claims, No Drawings

PROCESS FOR THE PRODUCTION OF FERMENTATION ETHANOL

This invention is concerned with a process for the production of ethanol by fermentation. In one aspect, this invention is concerned with an improvement in the fermentation process. In another aspect, this invention is concerned with an energy efficient process for ethanol production.

The production of alcoholic beverages by the fermentation of fruit and grains is of ancient origin. In more recent times, the isolation of ethanol in concentrated or in pure form for use either in beverages, in industry, or as fuel, has assumed considerable importance. In general, ethanol may be produced by the fermentation of simple sugars such as glucose and fructose and oligosaccharides such as sucrose. Such substances and mixtures thereof which, without prior chemical modification, are convertible to ethanol will be referred to herein as "fermentable carbohydrates". More complex carbohydrates such as starches and cellulosic materials also may be converted to ethanol by fermentation, but usually only after they are degraded to lower molecular weight sugars or related materials. The fermentation usually proceeds in an anaerobic environment, with production of carbon dioxide by-product. The Kirk-Othmer Encyclopedia of Chemical Technology, Third Edition, John Wiley and Sons, New York, N.Y., presents a condensed summary of the state of the art of producing and isolating fermentation-ethanol in Volume 9, at pages 352-361, which pages including the literature referred to therein are incorporated herein by reference as background material.

Regardless of the source of fermentable carbohydrate, the fermentation step itself is characterized by end-product inhibition. The conversion of sugar to ethanol ceases when the volume concentration of ethanol becomes toxic to the fermenting organism, often to approximately 12 vol %. The recovery of concentrated or anhydrous ethanol from such a dilute solution requires a very costly distillation step.

U.S. Pat. No. 3,732,326 to N. Y. Chen discloses that certain crystalline zeolites, for example ZSM-5, having a silica to alumina mol ratio of at least 35 and an adequately large pore size, selectively sorb a less polar compound from a mixture of that compound with a more polar liquid. In particular, such zeolites selectively sorb methanol or tertiary butanol from a water solution of such alcohol. The entire content of U.S. Pat. No. 3,732,326 and the references contained therein are herein incorporated by reference. U.S. Pat. No. 3,936,353, also to N. Y. Chen, discloses a method for directly converting ethanol in dilute solution, such as in a fermentation mixture, to gasoline or aromatic hydrocarbons.

The present invention provides an energy efficient process for the production of concentrated or substantially anhydrous ethanol from any fermented mixture that contains ethanol. The present invention further provides an improved fermentation process whereby the end-product inhibition characteristic of the fermentation step is suppressed so that in effect the fermentation proceeds substantially beyond the point at which the toxic concentration of ethanol is formed.

In essence, the present invention makes use of the unusual selective sorption properties of zeolites that have a silica to alumina mol ratio of at least 35, as more fully described in U.S. Pat. No. 3,732,326. It is generally known that crystalline zeolites are shape selective in that they sorb compounds having less than a prescribed critical diameter, and exclude more bulky molecules. Thus, a zeolite with an effective pore diameter of about 5 angstrom units will admit only normal paraffins such as n-hexane or molecules having the same critical diameter, and exclude all branched or cyclic molecules such as isobutane and cyclohexane. Thus, ethanol is effectively sorbed by all crystalline zeolites that have an effective pore opening of at least five angstroms. Crystalline zeolites such as ZSM-5 which have an elliptical pore opening with an effective pore diameter slightly more than five angstroms will sorb straight chain molecules that have a single methyl branch but in general will exclude from the inner sorption regions molecules of any complexity such as glucose, fructose, etc. Thus, one type of selectivity exhibited by crystalline zeolites depends strictly on the geometry of the molecules involved.

Zeolites which are found in nature, and many of the synthetic crystalline zeolites, are characterized by a low silica to alumina mol ratio in the range from unity up to at most 10. These show a definite affinity for polar molecules, and will selectively sorb water in preference to less polar materials. For purposes of the present invention, such zeolites are not to be considered useful. Certain synthetic zeolites, however, such as ZSM-5 and zeolite beta are characterized by very high silica to alumina ratios, and indeed some of the zeolites may be synthesized in an essentially alumina-free form. Such zeolites preferentially sorb the less polar compound from a mixture, and sometimes do so with great affinity. These zeolites are sometimes referred to as "hydrophobic" zeolites. As an illustration of this type of selectivity, a series of dilute ethanol solutions that contained from 5 to 10% ethanol were contacted with ZSM-5 having silica to alumina mol ratios greater than 1,500. On separation of the sorbent it was found that the ethanol concentrations were reduced by 57-86%, and that the zeolite had sorbed from 65-85 miligrams of ethanol per gram of zeolite. Zeolites with a silica to alumina mol ratio of at least 35 and an effective pore diameter of at least 5 Angstroms exhibit selectivity for non-polar molecules together with the shape selectivity described above.

In the broadest aspect of the present invention, it is contemplated to recover concentrated ethanol from any fermentation mixture that comprises dilute aqueous ethanol by contacting said mixture with, as sorbent, a substantially catalytically inactive crystalline zeolite having a silica to alumina mol ratio of at least 35 and an effective pore diameter of at least 5 Angstroms. The sorbent is subsequently separated from the fermentation mixture and the sorbed ethanol recovered in concentrated form by desorption, e.g., by displacement with a volatile hydrocarbon such as propane. The remaining fermentation mixture, which contains nutrients, enzymes and other useful components, may be fortified and recycled. The term "catalytically inactive", as more fully described hereinbelow, is intended to mean "catalytically inactive under sorption and desorption conditions."

In another aspect of the present invention, the fermentation of a fermentable carbohydrate is conducted with control of the concentration of the dilute aqueous ethanol by selective sorption on a substantially catalytically inactive crystalline zeolite having a silica to alumina mol ratio of at least 35. The control of the ethanol concentration is maintained, as will be evident to one skilled in the art of sorption, by the relative amounts of sorbent and of fermentation broth, and by the contact time allowed for sorption. The aqueous ethanol concentration maintained in the fermentation mixture for present purposes is at least 1% below the toxic level of the fermenting organism, and preferably at least 2% below that concentration. Depending on the particular fermentation system, values of 11 vol % or less may be chosen, such as 8% or 6% or less. By this method of control, the ethanol in the fermentation mixture is not allowed to build up to the point at which it retards or completely stops the fermentation process. As will be evident, the process of this invention allows the fermentation to proceed with the production of large qantities of ethanol without encountering end-product inhibition. Of course, the fermentation mixture must be adjusted to optimize the production of ethanol such as by providing sufficient fermentable carbohydrate to permit such result. In general, it is contemplated to produce, by the method of this invention, substantially greater amounts of alcohol than would form an ethanol solution of concentration toxic to the organism in the absence of said sorption step. It is contemplated, for example, to produce total ethanol equivalent to at least 14 vol %, and even greater, such as 30 vol % or more.

There are various ways in which the sorption step may be conducted. For example, the zeolite sorbent more fully described hereinbelow may be mixed with the fermentation broth ab initio, i.e., prior to innoculation with the yeast culture. Or, the fermentation may be commenced in the absence of sorbent and, when the desired limiting ethanol concentration is achieved, the fermentation broth may be circulated over a bed of sorbent to selectively remove a portion or all of the ethanol after which the concentration is again allowed to build up. Prior to said circulation, it is in many instances desirable to clarify the stream to be treated. Such clarification may be accomplished, for example, by decantation, or by filtration, or by centrifugation. Separated microorganisms and other solids may be recombined with the calrified stream after reduction of the ethanol content. Various means of contact of sorbent and fermentation broth may be devised, including contact through a vapor phase, some of which may be advantageous. In any case, the sorbent will effectively remove the ethanol as a highly concentrated solution contained in its pores. When operating in any of the above described ways, the sorbent will, of course, become exhausted when its pores become filled with alcohol, at which point it may be separated from the fermentation broth or clarified liquor and the ethanol desorbed and recovered. The desorption may be conducted in a number of different ways, such as by heating with or without vacuum, or stripping with an even less polar material such as propane, butane, isobutane, or other volatile hydrocarbon. In any case, the ethanol recovered from the crystalline zeolite sorbent will be either anhydrous or in highly concentrated form and will require substantially less energy for recovery than is required by the distillation process practiced at the present time.

It is contemplated that any fermentation designed to produce ethanol may be adapted to the present process. For example, molasses may be diluted to a mash containing about 10-20 wt. % sugar after the pH of the mash is adjusted to about 4-5 with mineral acid. It is innoculated with yeast and the fermentation is carried out at 20°-32° C. for about 1-3 days. The fermented beer, which typically contains about 8 wt. % ethanol is then passed over a fresh bed of crystalline zeolite sorbent to reduce the ethanol content to about 2 wt. %, after which additional molasses is added to the mixture and the fermentation continued with the production of additional alcohol. After several cycles, the fermentation mixture may become less productive for any of a number of reasons, such as the accummulation of old yeast cells, in which case the remaining alcohol may be recovered from it by distillation, or preferably by sorption by the method of this invention.

The sorbents useful in the present invention are crystalline zeolites that have a silica to alumina mol ratio of at least 35 and an effective pore diameter of at least 5 Angstroms as evidenced by the ability to sorb n-hexane. Such zeolites are capable of selectively sorbing ethanol from dilute solutions. Natural zeolites, in general, do not have a sufficiently high silica to alumina ratio for effective use. However, a natural zeolite such as mordenite or its synthetic counterpart may be dealuminized, thereby increasing its silica to alumina ratio to 35 or more as described in U.S. Pat. No. 3,551,353, and rendered hydrophobic and useful in the present invention. Or, as described in the literature, a synthetic zeolite such as Linde Y may be treated with silicon tetrachloride to induce isomorphic substitution of silicon for aluminum even to the extent of forming a substantially alumina-free analog of the zeolite. Any of the foregoing modified zeolites having the requisite silica to alumina ratio are contemplated as useful in this invention.

In recent years an unusual group of synthetic zeolites, exemplified by ZSM-5, has become known. These zeolites are usually prepared utilizing an organic nitrogen compound in the forming solution. The zeolites, as crystallized, have a silica to alumina mol ratio well in excess of 10, and therefore are believed to have no existing natural counterparts. The silica to alumina mol ratio of the as-formed crystals most often have a silica to alumina mol ratio in excess of 35, and if somewhat less, are easily converted to said form by steaming and alumina extraction. Furthermore, it is known that some of these zeolites such as ZSM-5, may exist in homologous forms having silica to alumina ratios in excess of 1000, and even higher, i.e., as substantially pure silica crystals. Members of the unusual group of synthetic zeolites include zeolite Beta, ZSM-5, ZSM-11, ZSM-12, ZSM-23, ZSM-35, ZSM-38, ZSM-48 and similar materials. All of these are useful in the present invention.

The silica to alumina mol ratio herein referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mol ratios of at least 35 are useful, it is preferred in some instances to use zeolites having substantially higher silica/alumina ratios, e.g. 200 and above. In addition, zeolites as otherwise characterized herein but which are substantially free of aluminum, that is zeolites having silica to alumina mol ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mol ratio of infinity) but which otherwise embody the characteristics disclosed.

The specific zeolites described above, when prepared in the presence of organic cations, usually contain occluded organic nitrogen compounds. Such crystals, prior to use as sorbents, are activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation.

Zeolite Beta is described in U.S. Pat. No. 3,308,069, the entire content of which is incorporated herein by reference, including particularly the x-ray diffration pattern contained therein.

ZSM-5 is described in greater detail in U.S. Pat. No. 3,702,886 and U.S. Pat. No. Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN: (0–1.5)M$_{2/n}$O: (0–2.0)Al$_2$O$_3$: (100)SiO$_2$ wherein:

M is at least one cation having a valence n; and

RN is a C$_1$–C$_{20}$ organic compound having at least one amine functional group of pK$_a$ ≧ 7.

It is recognized that, particularly when the composition contains tetrahedral framework aluminum, a fraction of the amine functional groups may be protonated. The doubly protonated form, in conventional notation, would be (RNH)$_2$O and is equivalent in stoichiometry to 2 RN+H$_2$O.

The characteristic X-ray diffraction pattern of the synthetic zeolite ZSM-48 has the following significant lines:

| Characteristic Lines of ZSM-48 | |
| --- | --- |
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W−S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mol ratios of oxides, falling within the following ranges:

| REACTANTS | | BROAD | PREFERRED |
| --- | --- | --- | --- |
| Al$_2$O$_3$/SiO$_2$ | = | 0 to 0.02 | 0 to 0.01 |
| Na/SiO$_2$ | = | 0 to 2 | 0.1 to 1.0 |
| RN/SiO$_2$ | = | 0.01 to 2.0 | 0.05 to 1.0 |
| OH$^-$/SiO$_2$ | = | 0 to 0.25 | 0 to 0.1 |
| H$_2$O/SiO$_2$ | = | 10 to 100 | 20 to 70 |
| H$^+$(added)/SiO$_2$ | = | 0 to 0.2 | 0 to 0.05 | wherein RN is a C$_1$–C$_{20}$ organic compound having amine functional group of pK$_a$ ≧ 7. The mixture is maintained at 80°–250° C. until crystals of the material are formed. H$^+$(added) is moles acid added in excess of the moles of hydroxide added. In calculating H$^+$(added) and OH values, the term acid (H$^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

It is to be understood that by incorporating by reference the foregoing patents to describe examples of specific crystalline zeolites with greater particularity, it is intended that identification of the therein disclosed crystalline zeolites be resolved on the basis of their respective X-ray diffraction patterns. As discussed above, the present invention contemplates utilization of such sorbents wherein the mol ratio of silica to alumina is essentially unbounded. The incorporation of the identified patents should therefore not be construed as limiting the disclosed crystalline zeolites to those having the specific silica to alumina mol ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

In addition to the synthetic zeolites noted above, natural zeolites may in some cases be modified without collapse of the crystal structure to impart a silica to alumina mol ratio of at least 35, as illustrated above by mordenite. It is contemplated, for example, that natural ferrierite may be so treated. All such crystalline zeolites provide useful sorbents for present purposes. Broadly, any natural or synthetic crystalline zeolite having a silica to alumina mol ratio of at least 35 and an effective pore diameter of at least 5 Angstroms as evidenced by its ability to sorb at least 3 wt. % n-hexane at 100 mm pressure at 25° C., and which is substantially catalytically inactive as more fully defined hereinbelow, provides a useful sorbent for the present invention.

In the preferred aspect of this invention, the zeolites useful as sorbents herein are selected as those having a crystal framework density, in the dry hydrogen form of not substantially below about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier, this paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of selective sorption.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

A group of synthetic crystalline zeolites particularly well suited as sorbents are zeolite Beta, ZSM-5, ZSM-11, ZSM-12, ZSM-23, ZSM-35 and ZSM-48. These zeolites in the as synthesized form usually have a silica to alumina mol ratio greater than 35 and, after calcination in air, they exhibit the required sorption capacity for normal hexane. Most if not all of these zeolites also exhibit a crystal density of not substantially below 1.6 grams per cubic centimeter, and therefore unusual stability in long-term use. Particularly preferred is ZSM-5.

Because the zeolites crystals usually have a very small particle size, it is useful to incorporate them with a matrix comprising another material resistant to the conditions employed in the process. Such matrix material is useful as a binder to form particles of average diameter from 50 microns to ¼ inch. Such size facilitates separation of the sorbent from the fermentation mixture and recovery of alcohol.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and matrix, on an anhydrous basis, may vary widely but preferably the zeolite content is made as high as is consistent with good attrition resistance and is usually in the range of about 20 to about 80 percent by weight of the dry composite.

We will now address the term "catalytically inactive" as used in the present context. It is generally recognized by those skilled in the art of catalysis that the structures herein described are highly effective catalysts for hydrocarbon conversions as well as other reactions. Most of these conversions are what would be recognized as "acid-catalyzed" reactions. In general, however, it is also recognized that such catalyzed conversions require a temperature of 300° C. or higher. However, the sorption and desorption steps contemplated in the present invention are conducted at temperatures well below 300° C., and in particular at temperatures from about 0° C. to about 200° C. Because of these low temperatures, any catalytic activity present is markedly diminished or entirely suppressed. The term "substantially catalytically inactive" as used herein is intended to mean substantially catalytically inactive under the specific sorption and desorption conditions chosen within the above prescribed temperature range. It further is intended to mean that the sorbent used under the chosen conditions is sufficiently inactive to permit recovery of at least 75 wt. % and preferably at least 90% of the sorbed ethanol without catalytic transformation to other products such as ethylene or diethyl ether.

The catalytic activity of the sorbent may be conveniently measured by its activity for cracking normal hexane at elevated temperatures. The measure of this activity related to a standard substance has been termed the "Alpha value", and the procedure for conducting this test and determining the Alpha value of a zeolite has been published in the Journal of Catalysis, Vol. VI, pp. 278–287 (1966) the entire content of this article and the method therein described are herein incorporated by reference. In general, if the sorption or desorption steps are to be conducted at a temperature of 100° C. to 200° C., it is desirable to employ, as sorbent, a form of the described zeolite having an Alpha value less than 50. With such sorbent, the requirement set forth above for substantial catalytic inactivity is met.

The Alpha values of the sorbents utilized in this invention become smaller as the silica to alumina mol ratio becomes greater. Thus, although sorbents with a silica to alumina ratio greater than 35 are useful in the present invention, it is preferred to use those sorbents that have a silica to alumina mol ratio of at least 70, and most preferred is to use sorbents for which the ratio is at least about 200. The sorbents described above may be in the hydrogen form or in a salt form which results, for example, when the sorbent is base exchanged with an alkali or alkaline earth metal hydroxide. The salt forms, in general, and particularly the alkaline metal forms, have reduced Alpha values and are better suited for use in the present invention than the hydrogen form. Thus, when the sorbent selected for use has a silica to alumina mol ratio less than 200, it is preferred to use the sorbent in the alkali or alkaline earth metal salt form, the alkali metal form as being preferred with the potassium form particularly preferred. These salt forms in general may be prepared such that the resulting sorbent has an Alpha value of 10 or less. It is also advantageous to use the salt forms for sorbents that have a silica to alumina ratio of at least about 200, although good results may be obtained with such sorbents even in the hydrogen form, especially when neither the temperature of sorption nor of desorption exceeds 100° C.

Separation and regeneration of spent sorbent with recovery of ethanol may be conducted by any known means. These include the use of vacuum with or without heating the sorbent to an elevated temperature; displacement with inert gas including carbon dioxide; and displacement with paraffins. Included as useful paraffins are propane, butane, isobutane, pentane and higher molecular weight paraffins. With the more volatile hydrocarbons such as with propane, it is contemplated to displace and recover the ethanol and thereafter to remove the sorbed propane displacing compound from the sorbent by reduction in pressure. Butane also may be used in such a "pressure swing" regeneration. The higher molecular weight hydrocarbons may be desorbed by heating at temperatures which may exceed 200° C., for example, temperatures up to 400° C. or higher.

It is a feature of this invention that sorbent which has lost efficiency after repeated cycles due to the accumulation of organic matter within the pores may be regenerated by burning at elevated temperatures such as at 450° to 650° C. This effects removal of any foreign organic matter and restores the sorbent to its initial effectiveness.

Attention is called to U.S. application entitled, "METHOD FOR PRODUCING CHEMICAL COMPOUNDS" filed on even date herewith.

What is claimed is:

1. In a process for the production of fermentation ethanol, which process comprises fermenting a fermentable carbohydrate thereby forming a fermented mixture comprising a dilute aqueous ethanol solution, the improvement consisting essentially of selectively sorbing ethanol from said fermented mixture with a crystalline zeolite sorbent having a silica to alumina mol ratio of at least 35 and an effective pore diameter of at least 5 Angstroms under conditions effective to sorb from at least about 10% to about 100% of said ethanol contained in said fermented mixture, separating said sorbent from said fermented mixture and desorbing sorbed ethanol from said sorbent.

2. The process described in claim 1 wherein said crystalline zeolite sorbent has a silica to alumina mol ratio of at least about 200.

3. The process described in claim 1 wherein said crystalline zeolite sorbent has a crystal density in the dry hydrogen form of not less than about 1.6 grams per cubic centimeter.

4. The process described in claim 1 wherein said crystalline zeolite sorbent is selected from the group consisting of zeolite Beta, ZSM-5, ZSM-11, ZSM-12, ZSM-23, ZSM-35 and ZSM-48.

5. The process described in claim 2 wherein said crystalline zeolite sorbent has a crystal density in the dry hydrogen form of not less than about 1.6 grams per cubic centimeter.

6. The process described in claim 2 wherein said crystalline zeolite sorbent is selected from the group consisting of zeolite Beta, ZSM-5, ZSM-11, ZSM-12, ZSM-23, ZSM-35 and ZSM-48.

7. The process described in claim 4 wherein said crystalline sorbent has a silica to alumina mol ratio of at least about 200.

8. The process described in claim 1 wherein said sorption and desorption steps are conducted at a temperature of about 0° to about 200° C.

9. The process described in claim 2 wherein said sorption and desorption steps are conducted at a temperature of about 0° to about 200° C.

10. The process described in claim 3 wherein said sorption and desorption steps are conducted at a temperature of about 0° to about 200° C.

11. The process described in claim 4 wherein said sorption and desorption steps are conducted at a temperature of about 0° to about 200° C.

12. The process described in claim 5 wherein said sorption and desorption steps are conducted at a temperature of about 0° to about 200° C.

13. The process described in claim 6 wherein said sorption and desorption steps are conducted at a temperature of about 0° to about 200° C.

14. Th process described in claim 7 wherein said sorption and desorption steps are conducted at a temperature of about 0° to about 200° C.

15. The process described in claim 1 or 2 or 3 or 4 or 5 or 6 or 7 or 8 or 9 or 10 or 11 or 12 or 13 or 14 wherein said crystalline sorbent is contained in a matrix.

16. In a process for the production of ethanol, which process includes the step of fermenting a fermentable carbohydrate thereby forming a fermented mixture comprising a dilute aqueous ethanol solution, said ethanol production ceasing when the concentration of said ethanol becomes toxic to the fermenting organism; the improvement which consists essentially of maintaining said concentration of ethanol in said solution at least about 1.0 vol % less than said toxic concentration by contacting said solution with a substantially catalytically inactive crystalline zeolite sorbent having a silica to alumina mol ratio of at least 35 which selectively sorbs said ethanol, and continuing said fermentation until a total amount of ethanol is produced which is substantially higher than said toxic concentration in the absence of said sorption step whereby the efficiency of the process is increased.

17. The process described in claim 16 wherein sorbed ethanol is desorbed are recovered from said sorbent.

18. The process described in claim 17 wherein said crystalline zeolite sorbent has a silica to alumina mol ratio of at least about 200.

19. The process described in claim 16 wherein said crystalline zeolite sorbent is selected from the group consisting of zeolite Beta, ZSM-5, ZSM-11, ZSM-12, ZSM-23, ZSM-35 and ZSM-48.

20. The process described in claim 18 wherein said crystalline zeolite sorbent is selected from the group consisting of zeolite Beta, ZSM-5, ZSM-11, ZSM-12, ZSM-23, ZSM-35 and ZSM-48.

21. The process described in claim 18 wherein said sorbing and desorbing steps are conducted at a temperature of about 0° to about 200° C.

22. The process described in claim 16 or 17 or 18 or 19 or 20 or 21 wherein said crystalline zeolite sorbent is contained in a matrix and is in the alkali metal form.

23. The process described in claim 16 or 17 or 19 or 20 or 21 wherein said crystalline zeolite sorbent is substantially free of alumina.

24. The process described in claim 16 wherein said selective sorption of said ethanol is effected through the vapor phase.

25. The process described in claim 16 including the step of clarifying at least a portion of said fermented mixture and wherein said selective sorption of said ethanol is effected by contacting said catalytically inactive crystalline zeolite sorbent with said clarified fermented mixture.

26. The process of claim 16 wherein the total amount of ethanol produced is at least 14 vol %.

27. The process of claim 16 wherein the total amount of ethanol produced is at least 30 vol %.

28. The process of claim 1 or 16 wherein said fermented mixture is obtained by adjusting a molasses mash to a pH of about 4–5 with mineral acid, diluting said molasses to about 10–20 wt.% sugar content, innoculating the resulting mash with yeast, and fermenting the innoculated mash at temperatures of 20°–32° C. for about 1 to 3 days.

* * * * *